United States Patent [19]
Mitchell

[11] Patent Number: 4,891,044
[45] Date of Patent: Jan. 2, 1990

[54] OPHTHALMIC ASPIRATING/IRRIGATING DEVICE

[75] Inventor: David Mitchell, Redditch, England

[73] Assignee: Coats Viyella Medical Limited, Worcestershire, England

[21] Appl. No.: 141,604

[22] PCT Filed: May 1, 1987

[86] PCT No.: PCT/GB87/00291
§ 371 Date: Jan. 4, 1988
§ 102(e) Date: Jan. 4, 1988

[87] PCT Pub. No.: WO87/06455
PCT Pub. Date: Nov. 5, 1987

[30] Foreign Application Priority Data

May 3, 1986 [GB] United Kingdom ............... 8610896

[51] Int. Cl.$^4$ ............................................. A61M 1/00
[52] U.S. Cl. ...................................... 604/27; 604/36; 604/35
[58] Field of Search .................. 604/27, 30, 35, 36, 604/38, 39, 43, 44, 48, 54

[56] References Cited
U.S. PATENT DOCUMENTS

| 3,818,907 | 6/1974 | Walton | 604/38 |
| 4,014,333 | 3/1977 | McIntyre | 604/43 |
| 4,084,606 | 4/1978 | Hleman | 604/30 |

Primary Examiner—Jerome L. Kruter
Attorney, Agent, or Firm—Larson and Taylor

[57] ABSTRACT

An ophthalmic aspirating/irrigating device incorporates a needle comprising two tubes disposed in close proximity and terminating close to one another at the distal end of the device. The distal end of the needle is insertable into an eye to be treated while the proximal end of one tube is connected to a syringe by way of a valve device. The valve device contains two one way valves, one of which provides passage only from the syringe to a discharge opening and the second of which provides passage only in the direction from the tube to the syringe. The valves are of the type comprising two flexible lips normally in contact with one another and separable by a pressure rise across the valve to present an orifice. The valves are disposed such that when the device is in a vertical position with the needle projecting downwardly, the orifice of the one valve is located at a distance of at most 1 mm below the level of the orifice of the other valve.

3 Claims, 1 Drawing Sheet

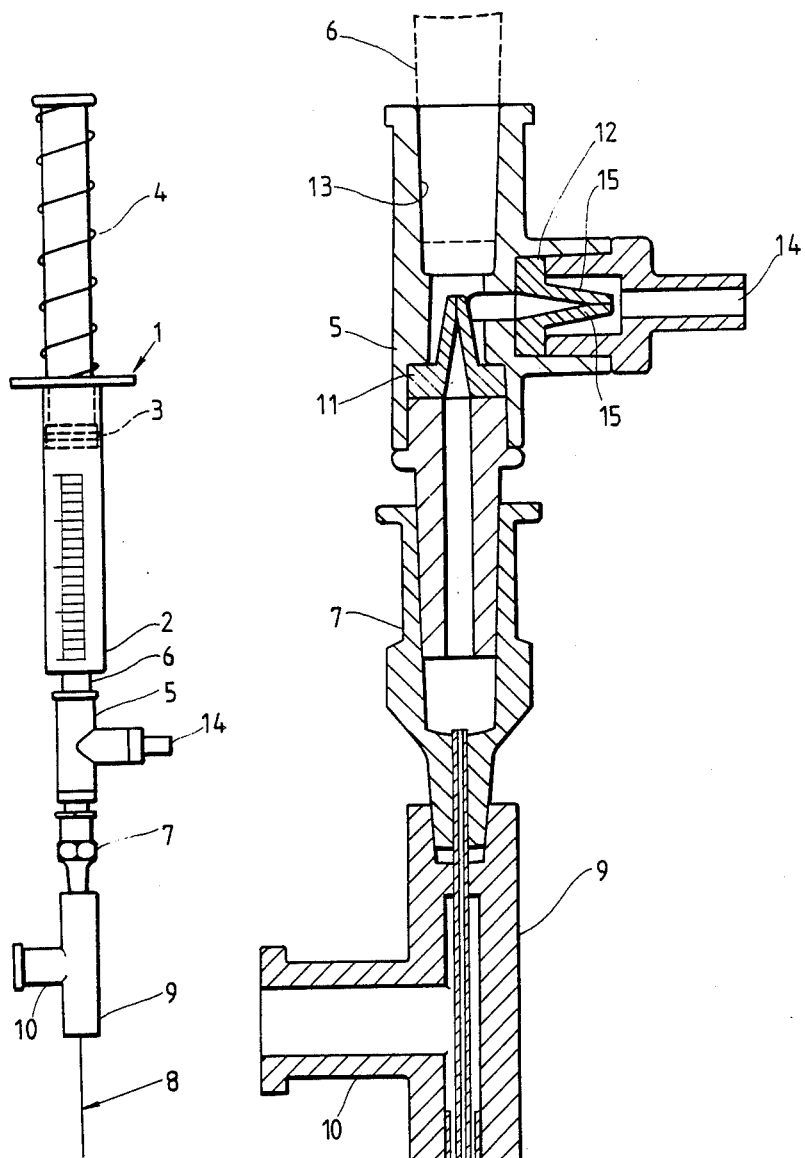

OPHTHALMIC ASPIRATING/IRRIGATING DEVICE

FIELD OF THE INVENTION

The invention relates to an ophthalmic aspirating/irrigating device.

BACKGROUND OF THE INVENTION

In the performance of some operations to the eye it is necessary to remove cortical fragments and/or other débris from behind the iris, such action being preferably followed by an irrigating action in which irrigating fluid is introduced behind the iris to ensure that the place from which the cortical fragments had been removed is clear. The instrument which has been developed to perform this operation comprises a syringe attached to a double needle having two passages one of which is open at the proximal end to the barrel of the syringe and the other of which is connectible at the proximal end to a source of supply of irrigating liquid and the distal ends of the two passages are open and close to one another. In operation of the aspirating/irrigating device the piston of the syringe is advanced and the distal end of the double needle is introduced into the eye and maneuvered into the position in which the distal end of the needle is in the portion of the eye containing the cortical fragments and/or other débris. Irrigating liquid is allowed to flow into the eye cavity containing the débris and the piston of the syringe is then withdrawn to draw the irrigating liquid containing the cortical fragments and/or other débris through the tube connected to the barrel of the syringe. It usually happens that at the first withdrawal of the plunger not all the débris is removed and it may be necessary to remove the device from the eye several times so that débris which has been withdrawn from the eye may be discharged from the syringe along with irrigating liquid, the needle then being reinserted into the eye to remove remaining débris. It has been found that this action may have to be performed as often as three or four times.

The repeated insertion of a needle into the eye is highly undesirable and it is an object of the present invention to provide an aspirating/irrigating device which requires only one insertion into an eye to remove all the débris and irrigate the eye.

SUMMARY OF THE INVENTION

In accordance with invention, an ophthalmic aspirating/irrigating device is provided having, in use, a distal end and a proximal end and comprising a needle comprising two tubes disposed in close proximity, and terminating at one end close to one another at the distal end of the device, said one end of said tubes being insertable into an eye to be treated; and valve means connecting the other end of one tube to a syringe, said valve means comprising a first one way valve which provides passage only from the syringe to a discharge opening of the device and a second one way valve which provides passage only in the direction from said one tube to the syringe, each of said valves comprising two flexible lips normally in contact with one another and separable by a pressure rise across the valve to present an orifice, and said valves being so disposed that when the device is in a vertical position with the needle projecting downwardly, the orifice of said first valve is located a distance of at most 1 mm below the level of the orifice of said second valve.

The invention also comprises the combination of a device as described and a syringe to which the device is fitted.

Each one way valve may be formed as two flexible lips which are normally in contact with one another and forming together an acute angle so that the lips can be moved apart by a pressure rise across the valve in one direction and will be forced together by a pressure rise across the valve in the other direction.

The two valves may be incorporated within a body having a straight tubular portion containing the valve providing one way access from the needle tube to the syringe and a branch containing the valve providing one way access from the syringe to a discharge opening.

For a reason to be explained later it is important to locate the valves such that when the device is in a vertical position with the needle projecting downwardly the tip of the valve providing passage only from the syringe to the discharge opening is located a distance below the level of the tip of the other valve providing passage only in the direction from the needle tube to the syringe. Said distance may be about 1 mm or less.

The straight tubular portion may be so arranged that the end adjacent the downstream end of the one way valve in said straight portion is a push fit on the nozzle of a syringe while the other end is formed as a spigot which is a push fit on a socket carrying the needle.

For ease both of manufacture and assembly all the parts of the valve device may be moulded to be a push fit in one another.

BRIEF DESCRIPTION OF THE DRAWINGS

A practical embodiment of the invention is illustrated in the accompanying drawings in which FIG. 1 shows a device according to the invention fitted to a surgical syringe and FIG. 2 is a section of the device of the invention drawn to a much enlarged scale.

DESCRIPTION OF THE PREFERRED EMBODIMENT

In the drawings 1 denotes a syringe incorporating a barrel 2 and a plunger 3 loaded by a spring 4 fitted as an addition to the syringe so that the plunger 3 tends to move to its withdrawn position. 5 denotes a valve device attached to the nozzle 6 of the syringe 1. 7 denotes a socket a press fit on the end of the valve device 5 remote from that arranged to receive the nozzle 6 of the syringe. The socket 7 supports the inner tube 8A of a needle 8 which comprises said inner tube 8A and an outer tube 8B surrounding the inner tube 8A. The inner tube 8A which is open at its distal end, i.e. the end remote from the socket 7, is thus connected through the socket 7 and by way of the valve device 5 to the interior of the barrel 2 of the syringe 1. The outer tube 8B terminates slightly short of the inner tube 8A at the distal end of the needle 8 and is open to the interior of a sleeve 9 formed with a branch connection 10 connectible to a supply of irrigating liquid. The valve device 5 incorporates two one way valves 11 and 12 so arranged that the valve 11 provides passage only in a direction towards the syringe. The nozzle 6 of the syringe 1 fits into the socket 13 provided in the valve device 5. The valve 12 is arranged in the branch of the valve device and is so arranged that it provides passage only in the direction from the interior of the valve device to a discharge passage 14. Each valve comprises two lips 15 of flexible material which come together at an acute angle and are arranged to be normally in contact with one another, being maintained in contact by their own resilience.

In practice, when the device is to be used on an eye it is fitted as described to a surgical syringe and the branch connection 10 is connected to a supply of irrigating fluid. The plunger 3 of the syringe is first advanced and the needle 8 is then inserted into the eye usually with the distal end in the space behind the iris where cortical fragments and other débris tend to gather. Irrigating fluid passes through the tube 8B in the annulus between the tubes 8A and 8B into said space behind the iris. On releasing the plunger the spring 4 withdraws the plunger and the suction in the barrel 2 causes the valve 11 to open i.e. the two lips 15 separate and irrigating fluid which is now filling said space behind the iris and cortical fragments and other débris are sucked from the eye into the syringe barrel through the tube 8A. When the plunger has been withdrawn to its fullest extent it is again advanced compressing the spring 4. This time the rise of pressure in the barrel 2 causes the lips 15 of the valve 11 to come together rapidly although they tend to do so anyway by their own resilience as soon as pressure is equalized on both sides of the valve. At the same time the rise of pressure on the upstream side of the valve 12 causes the lips 15 of the valve 12 to open so that the irrigating fluid and fragments and débris in the syringe are expelled through the valve 12 and out of the discharge passage 14. Without removing the device from the eye the plunger may now be released for a second time so that irrigating fluid and other cortical fragments and débris which had not been removed from the eye in the first operation are withdrawn into the syringe barrel 2 and then expelled as before through the passage 14. This operation may be performed as often as is necessary until no more cortical fragments and débris remain in the eye. The device is removed from the eye only when the operation is complete, i.e. when all cortical fragments and débris are removed. The operation can thus be performed with only one insertion of the syringe into the eye.

It is sometimes found during use of the instrument when withdrawing irrigating liquid and any fragments of débris that the suction created causes the posterior chamber capsule of the eye, usually referred to as the capsular bag, to be sucked against the orifice of the needle. Withdrawal of the liquid and contained fragments must be stopped immediately so that damage to the capsular bag does not occur. The capsular bag must then be moved away from the needle to clear the needle orifice. This cannot normally be done by merely depressing the plunger of the syringe because the rise of pressure would simply close the valve 11 so that no pressure would be applied from within the needle, also the slight pressure of the irrigating liquid entering through the branch connection 10 is sufficient to keep the capsular bag pressed against the needle. To avoid such a happening the tip of the discharge valve 12 is located a distance below the level of the tip of the inlet valve 11 an amount which is not more than 1 mm. By this expedient it is possible by momentarily depressing the plunger by a minute extent 30 to generate a small pressure wave which passes through the valve 11 before it has had time to close and, since the valve 11 is above the level of the valve 12 and thus receives the pressure wave a small fraction of a second before the valve 12 receives the pressure wave, before the valve 12 has had time to open and nullify the effect. This extremely small rise of pressure momentarily occurring within the tube 8A is sufficient to move the capsular bag away from the orifice in the needle without damage to the capsular bag. The operation of removing cortical fragments and debris may then be continued.

The ophthalmic device of the invention particularly incorporating two valves as illustrated has been found to be very effective because of the feature that an extremely small pressure difference across each valve causes it either to open or close according to the side on which pressure is higher. There is thus immediate response by the valves to movement of the piston 3 and also virtually no reverse flow through the valves. Other types of valves tend to be slower in action and also to permit some amount of reverse flow so that cortical fragments and débris removed from the eye can be forced back into the eye. It may be remarked that the plunger withdrawal spring has been fitted to the syringe so that the syringe may be operated with one hand. This is highly desirable in eye operations. The device may however be used without the addition of a plunger withdrawal spring.

I claim:

1. An ophthalmic aspirating/irrigating device having, in use, a distal end and a proximal end and comprising a needle comprising two tubes disposed in close proximity, and terminating at one end close to one another at the distal end of the device, said one end of said tubes being insertable into an eye to be treated; and a valve assembly connected between the other end of one tube and a syringe including a plunger, said valve assembly comprising a first one way valve means, comprising two flexible lips normally in contact with one another and separable by a pressure rise across the first valve means to present a first orifice, for providing passage only from the syringe to a discharge opening of the device and a second one way valve means, comprising two flexible lips normally in contact with one another and separable by a pressure rise across the second valve means to present a second orifice and disposed relative to said first valve means such that when the device is in a vertical position with the needle projecting downwardly the orifice of said first valve means is located at a distance of at most 1 mm below the level of the orifice of said second valve means, for normally providing passage only in the direction from said one tube to the syringe and for also providing passage of a small pressure wave, produced by momentarily depressing the plunger of the syringe, through the second valve means prior to the closing of said second valve means and the opening of the first valve means.

2. A device according to claim 1 wherein the two valves are incorporated within a body having a straight tubular portion containing the first valve and a branch containing the second valve.

3. A device according to claim 2, wherein the straight tubular portion is so arranged that the end adjacent the downstream end of the one way valve in said straight portion is a push fit on a nozzle portion of the syringe while the other end is formed as a spigot which is a push fit on a socket carrying the needle.

* * * * *